United States Patent [19]
Koiso et al.

[11] Patent Number: 6,127,294
[45] Date of Patent: Oct. 3, 2000

[54] SHEET SHAPED HEAT GENERATING BODY AND METHOD OF MANUFACTURING SAME

[75] Inventors: Yasuhiko Koiso; Naoto Wagatsuma; Mamoru Takahashi, all of Hiratsuka, Japan

[73] Assignee: Japan Pionics Co., Ltd., Tokyo, Japan

[*] Notice: This patent is subject to a terminal disclaimer.

[21] Appl. No.: 09/029,071

[22] PCT Filed: Jul. 2, 1997

[86] PCT No.: PCT/JP97/02289

§ 371 Date: May 14, 1998

§ 102(e) Date: May 14, 1998

[87] PCT Pub. No.: WO98/00077

PCT Pub. Date: Jan. 8, 1998

[30] Foreign Application Priority Data

Jul. 2, 1996 [JP] Japan ..................................... 8-191326

[51] Int. Cl.[7] ................................. D04H 3/12; A61F 7/00
[52] U.S. Cl. ........................... 442/327; 442/72; 442/284; 442/286; 442/290; 442/389; 442/393; 156/145; 427/381
[58] Field of Search ........................... 428/327; 156/145; 427/381; 442/72, 284, 286, 290, 389, 393, 327; 126/204, 249.02

[56] References Cited

U.S. PATENT DOCUMENTS

| | | | |
|---|---|---|---|
| 4,496,415 | 1/1985 | Sprengling | 156/283 |
| 5,425,975 | 6/1995 | Koiso et al. | 428/74 |
| 5,472,541 | 12/1995 | Simmons et al. | 156/231 |
| 5,975,074 | 11/1999 | Koiso et al. | 126/204 |

FOREIGN PATENT DOCUMENTS

| | | |
|---|---|---|
| 0 271 278 | 12/1987 | European Pat. Off. . |
| 0 370 600 | 5/1990 | European Pat. Off. . |
| 53-14185 | 2/1978 | Japan . |
| 56-33980 | 7/1981 | Japan . |
| 62-011528 | 1/1987 | Japan . |
| 2-142561 | 5/1990 | Japan . |
| 3-152894 | 6/1991 | Japan . |
| 4-59904 | 9/1992 | Japan . |
| 7-59809 | 3/1995 | Japan . |
| 8-112303 | 5/1996 | Japan . |
| 8-173471 | 7/1996 | Japan . |
| 0 427 475 A1 | 5/1991 | WIPO . |
| 96/11654 | 4/1996 | WIPO . |

OTHER PUBLICATIONS

Int'l Search Report, Nov. 1999.

*Primary Examiner*—Terrell Morris
*Assistant Examiner*—John J. Guarriello
*Attorney, Agent, or Firm*—Nixon Peabody LLP; Thomas W. Cole

[57] ABSTRACT

The present invention provides a warmer in the form of a sheet shaped heat generating body which is obtained using a warming composition that generates heat when in contact with air, in which the warming composition can be easily dispersed and held in a uniform arrangement, and in which the warming composition is prevented from leaking; and provides a method for manufacturing such a sheet. The sheet shaped heat generating body pertaining to the present invention is obtained by supporting a warming composition and a heat-fusible adhesive powder on a nonwoven fabric (a), superposing a nonwoven fabric (b) on the upper surface, heating and pressing the assembly with the aid of a molding press, and impregnating the resulting sheet with water or an aqueous solution of an inorganic electrolyte.

17 Claims, 1 Drawing Sheet

SHEET SHAPED HEAT GENERATING BODY AND METHOD OF MANUFACTURING SAME

TECHNICAL FIELD

The present invention relates to a sheet shaped heat generating body and to a method for manufacturing such a sheet and, more particularly, to a thin and flexible sheet shaped heat generating body whose warming composition does not move or shift during use, and to a method for manufacturing such a sheet.

BACKGROUND ART

Warmer packs obtained by placing a warming composition containing, within a breathable pack, iron powder or other oxidizable metal powder (warming means) as its principal component and generating heat when brought into contact with the oxygen in the air, are widely used as pocket heaters or the like.

Such warmers, while simple to use, are still disadvantageous in that the warming composition is shifted to the bottom of the pack by gravity not only during movement but also in a stationary state when worn on the body, creating discomfort due to a change in shape and adversely affecting performance due to a change in the heat-generating capabilities themselves.

Various attempts have been made to support or sandwich the warming composition with a support material or the like as a means to address these problems.

Examples include (1) a method in which a plurality of pieces of nonwoven fabric made of heat-fused fibers containing vegetable fibers are superposed, and a chemical warming agent is dispersed therein (Japanese Laid-Open Patent Application 2-142561), (2) a method in which a warming agent is dispersed and held on a support sheet having numerous voids (Japanese Laid-Open Patent Application 3-152894), and (3) a method in which a piece of nonwoven fabric having a denser structure is superposed using an adhesive on the lower surface of a nonwoven fabric having numerous voids, a powdered warming composition is dispersed and fixed, another piece of nonwoven fabric is superposed on the uppermost surface thereof, and the assembly is heated and compressed with the aid of a mold press (Japanese Laid-Open Patent Application 8-112303).

However, these methods have the following drawbacks related to the manufacture of a sheet shaped heat generating body and to the resulting sheet shaped heat generating body.

Method 1 is disadvantageous in that combining a plurality of nonwoven fabrics by utilizing the water retentivity of vegetable fibers and the heat fusion properties of synthetic fibers requires complex structuring and processing; fails to adequately bond the nonwoven fabrics when certain types of heat-fusible fibers are used, certain amounts of materials are blended and spun, or the like; and sometimes makes it difficult to form sheet shaped heat generating bodies. Another drawback is that a stiff network structure results and the flexibility is lost when nonwoven fabrics are thoroughly fused under heat.

In the case of method 2, in which a warming composition is dispersed and fixed on a support sheet having numerous voids, it is difficult to securely hold the powder in the voids, and, depending on the porosity of the support sheet, the warming agent sometimes pierces the support sheet and leaks out through the lower surface, or the powder penetrates too deeply into the voids and remains on the upper surface, causing powder leakage.

In the case of method 3, in which a warming composition is supported on a piece of nonwoven fabric having numerous voids, and another piece of nonwoven fabric is superposed on the upper surface thereof, the warming composition does not leak out from the nonwoven fabric, but adhesion between the pieces of nonwoven fabric is inadequate, the layers sometimes separating from each other during fabrication, and the powder leaking out from between the layers of nonwoven fabric in certain applications.

The above situation created a need for the development of a flexible sheet shaped heat generating body and a need for the development of a method for manufacturing such a sheet in which the warming composition can be easily dispersed and held in a uniform configuration, and the warming composition is prevented from leaking.

SUMMARY OF THE INVENTION

As a result of painstaking research aimed at addressing the aforementioned problems, the inventors perfected the present invention upon discovering that these drawbacks can be overcome by adopting an approach in which a heat-fusible adhesive powder is dispersed and held together with a powdered warming composition inside the voids of a piece of nonwoven fabric, another piece of nonwoven fabric then being superposed on the upper surface of the nonwoven fabric, and the assembly being heated and compressed.

Specifically, the present invention provides a sheet shaped heat generating body wherein a nonwoven fabric (b) is superposed on the lower surface of a nonwoven fabric (a) having numerous voids, a nonwoven fabric (c) is superposed on the upper surface of the nonwoven fabric (a), a powdered warming composition and a heat-fusible adhesive powder are held in the voids of the nonwoven fabric (a) and nonwoven fabric (c) and between the superposed layers of the nonwoven fabric (a) and nonwoven fabric (c), the nonwoven fabric (a) and nonwoven fabric (c) are bonded by being heated and compressed with the aid of a heating and compressing apparatus, and the assembly is impregnated with water or an aqueous solution of an inorganic electrolyte.

The present invention also provides a sheet shaped heat generating body wherein a powdered warming composition and a heat-fusible adhesive powder are held in the voids of a nonwoven fabric (a) and a nonwoven fabric (c) and between the superposed layers of the nonwoven fabric (a) and nonwoven fabric (c), the nonwoven fabric (a) and nonwoven fabric (c) are bonded by being heated and compressed with the aid of a heating and compressing apparatus, and the assembly is impregnated with water or an aqueous solution of an inorganic electrolyte.

The present invention further provides a sheet shaped heat generating body wherein a plurality of pieces of nonwoven fabric having numerous voids are superposed, a powdered warming composition and a heat-fusible adhesive powder are held in at least one layer of nonwoven fabric, at least one side is bonded to the other piece of nonwoven fabric in contact with this layer of nonwoven fabric by being heated and compressed with the aid of a heating and compressing apparatus, and the assembly is impregnated with water or an aqueous solution of an inorganic electrolyte.

The present invention additionally provides a method for manufacturing a sheet shaped heat generating body comprising steps in which a nonwoven fabric (b) is superposed on the lower surface of a nonwoven fabric (a) having numerous voids, these nonwoven fabrics are bonded using water or an adhesive, a powdered warming composition and a heat-fusible adhesive powder are spread over the upper surface of the nonwoven fabric (a) and held inside its voids, a nonwoven fabric (c) is subsequently superposed on the upper surface of the nonwoven fabric (a), the nonwoven fabric (a) and nonwoven fabric (c) are bonded by being heated and compressed with the aid of a heating and compressing apparatus, and the assembly is then impregnated with water or an aqueous solution of an inorganic electrolyte.

Moreover, the present invention provides a method for manufacturing a sheet shaped heat generating body comprising steps in which a powdered warming composition and a heat-fusible adhesive powder are spread over the upper surface and held in the voids of a nonwoven fabric (a) which has numerous voids and whose lower surface is optionally covered with adhered water, a nonwoven fabric (c) is superposed on the upper surface of the nonwoven fabric (a), the nonwoven fabric (a) and nonwoven fabric (c) are bonded by being heated and compressed with the aid of a heating and compressing apparatus, and the assembly is impregnated with water or an aqueous solution of an inorganic electrolyte.

The aforementioned heat-fusible adhesive powder may be at least one resin powder selected from the group consisting of homopolymers of thermoplastic resins selected from the group consisting of ionomers, ethylene/vinyl acetate copolymers, polyethylene, polypropylene, polystyrene, polyvinyl alcohol, methyl cellulose, and ethyl cellulose; polymer blends of these thermoplastic resins; and hot melts containing these thermoplastic resins as their base polymers.

In addition, the softening point of the aforementioned heat-fusible adhesive powder may be set to 40°200° C. Furthermore, the amount in which the aforementioned heat-fusible adhesive powder is added may be set to 0.1–20.0 parts by weight per 100 parts by weight of the oxidizable metal powder.

Moreover, the aforementioned powdered warming composition may contain an oxidizable metal powder and activated carbon, or an oxidizable metal powder, activated carbon, and an inorganic electrolyte as its principal components.

At least one of the pressure surfaces of the aforementioned heating and compressing apparatus is embossed.

The aforementioned nonwoven fabrics (a), (b), and (c) may have at least one component selected from the group consisting of pulp, cotton, jute, rayon, and acetate as their principal component.

DESCRIPTION OF THE PREFERRED EMBODIMENTS

Figure 1:
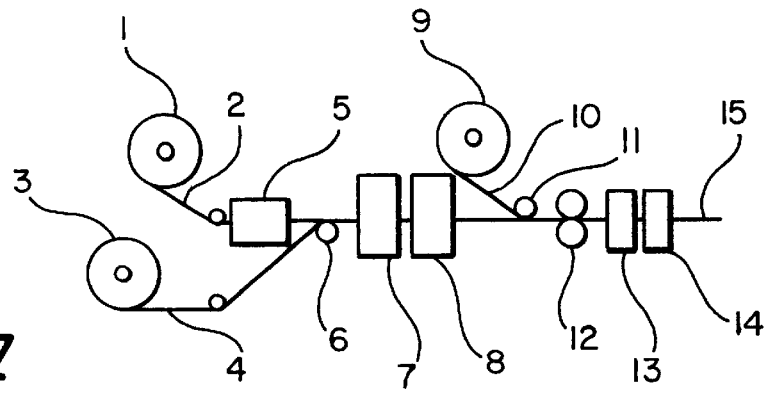
FIG. 1 is a schematic depicting the method for manufacturing a sheet shaped heat generating body in accordance with an embodiment of the present invention.

The present invention is applicable to warmers used for warming the human body, plants and animals, foodstuffs, mechanical implements, and the like; and to a method for manufacturing such warmers.

The present invention resides in a sheet shaped heat generating body wherein a nonwoven fabric (b) is superposed on the lower surface of a nonwoven fabric (a) having numerous voids, a heat-fusible adhesive powder and a powdered warming composition are dispersed on the upper surface of the nonwoven fabric (a), a nonwoven fabric (c) is superposed on the upper surface of this nonwoven fabric (a), a sheet is then formed by heating and compressing the assembly with the aid of a heating and compressing apparatus, and the assembly is subsequently impregnated with water or an aqueous solution of an inorganic electrolyte; and in a method for manufacturing such a sheet.

The warmer pertaining to the present invention is a sheet shaped heat generating body that has high flexibility and delivers an excellent heat-generation performance without causing the powdered warming composition to leak or the layers of nonwoven fabric to separate.

Furthermore, the method for manufacturing a warmer in accordance with the present invention yields an excellent shape retention effect for the sheet as a result of the fact that pieces of nonwoven fabric are partially bonded by a heat-fusible adhesive powder, and produces a sheet shaped heat generating body with excellent characteristics in terms of fabrication steps, such as the absence of layer separation or the leakage of the powdered warming composition.

The nonwoven fabric (a) used in this case has numerous voids. This fabric is flexible, has good water retentivity, and retains, in its voids, mixtures (hereinafter "powdered warming compositions") containing powdered starting material warming compositions that evolve heat when in contact with air. A nonwoven fabric obtained from vegetable fibers (such as pulp, cotton, or jute), regenerated fibers (such as rayon), or semisynthetic fibers (such as acetate), which may be used individually or as mixtures, is used as the nonwoven fabric (a). It is also possible to use nonwoven fabrics containing, in addition the above-described fibers, materials such as synthetic fibers (nylon, acrylic, polyurethane, polyethylene, polypropylene, and the like), as well as synthetic resins and natural resins commonly used as binders for nonwoven fabrics, provided these materials cannot be fused by heat. There is the danger, however, that water retentivity will decline, the fibers themselves will be fused, and the entire sheet will stiffen if such synthetic fibers or mixtures of synthetic fibers and natural resins are contained in large amounts. Therefore, the nonwoven fabric (a) used in the present invention is a nonwoven fabric containing vegetable fibers (such as pulp, cotton, or jute), regenerated fibers (such as rayon), and semisynthetic fibers (such as acetate) as its principal components, and this nonwoven fabric is not fused when heated.

The porosity of the nonwoven fabric (a) is commonly 70–99.5%, and preferably 80–99%, because higher porosity makes it easier to disperse the powdered warming composition in the voids.

The thickness of the nonwoven fabric (a), while varying with the porosity of the nonwoven fabric (a) and the amount in which the powdered warming composition is retained, is commonly 0.5–15 mm, and preferably 1–10 mm. Its weight is commonly 20–200 g/m$^2$, and preferably 30–150 g/m$^2$.

Nonwoven fabric (b) is designed to prevent the powdered warming composition from leaking through the nonwoven fabric (a). A fabric with high water retention and a denser structure than in nonwoven fabric (a) is commonly used. A nonwoven fabric obtained from vegetable fibers (such as pulp, cotton, or jute), regenerated fibers (such as rayon), and semisynthetic fibers (such as acetate), which may be used individually or as mixtures, is employed as the nonwoven fabric (b). It is also possible to use nonwoven fabrics containing, in addition to the above-described fibers, materials such as synthetic fibers (nylon, acrylic, polyurethane, polyethylene, polypropylene, and the like), as well as synthetic resins and natural resins commonly used as binders for nonwoven fabrics, provided these materials cannot be fused by heat. There is the danger, however, that water retentivity will decline, the fibers themselves will be fused, and the entire sheet will stiffen if such synthetic fibers or mixtures of synthetic fibers and natural resins are contained in large amounts. Therefore, the nonwoven fabric (b) used in the present invention is a nonwoven fabric, tissue paper, or other paper product containing vegetable fibers (such as pulp, cotton, or jute), regenerated fibers (such as rayon), and semisynthetic fibers (such as acetate) as its principal components, and this nonwoven fabric is not fused when heated.

The weight of the nonwoven fabric (b) is commonly 10–150 g/m$^2$, and preferably 20–100 g/m$^2$.

Nonwoven fabric (c) should preferably have voids and be able to retain water because this fabric is designed to hold the powdered warming composition that is released by the nonwoven fabric (a) but is retained by the upper surface of the nonwoven fabric (a), making it possible to prevent the powdered warming composition from leaking through the upper surface. In this case, it is possible to use the same starting material as that used for the nonwoven fabric (a). In particular, materials containing highly water-retentive vegetable fibers, regenerated fibers, and semisynthetic fibers as their principal components should preferably be used, and pulp, cotton, jute, rayon, acetate, and the like are particularly preferred.

Because of the danger that the powder will leak if the porosity of the nonwoven fabric (c) is too high, it is desirable for the porosity to be somewhat lower than that of the nonwoven fabric (a), usually 60–99.5%, and preferably 70–99%.

The thickness of the nonwoven fabric (c), while varying with its porosity and the amount in which the warming composition is retained, is commonly 0.2–7 mm, and preferably 0.5–5 mm. Its weight is commonly 10–150 g/m$^2$, and preferably 20–100 g/m$^2$.

The starting materials that constitute the powdered warming composition are an oxidizable metal powder, activated carbon, and an inorganic electrolyte. The inorganic electrolyte is a component of the powdered warming composition when mixed with the aforementioned starting materials in solid form, and is separate from the powdered warming composition when used for impregnation as an aqueous solution following sheet formation.

Iron powder, aluminum powder, or the like may be used as the oxidizable metal powder. Iron powder is commonly used, and reduced iron powder, atomized iron powder, electrolytic iron powder, or the like is preferred.

The activated carbon is used as a reaction aid and water-retaining agent. Coconut husk carbon, wood flour carbon, peat carbon, or the like is commonly used. A chloride of an alkali metal, alkaline-earth metal, or heavy metal is preferred for use as the inorganic electrolyte, as is an alkali metal sulfate. Examples include sodium chloride, potassium chloride, calcium chloride, magnesium chloride, ferric chloride, and sodium sulfate.

The warming composition is obtained by further admixing water or an aqueous solution of the inorganic electrolyte into the aforementioned powdered warming composition.

The powdered warming composition contains at least 50% of particles whose size is commonly no more than 60 mesh, and preferably no more than 100 mesh.

The mixing ratios of the components of the warming composition cannot be defined unconditionally and vary with the properties of the nonwoven fabric, the heat-generation characteristics to be obtained, and the like. For example, activated carbon, an inorganic electrolyte, and water may be used in amounts of 5–20 parts by weight, 1.5–10 parts by weight, and 25–60 parts by weight, respectively, per 100 parts by weight of oxidizable metal powder.

Water-retaining agents (such as pearlite powder, vermiculite, and super absorbent polymers), hydrogen production inhibitors, consolidation suppressants, and the like may also be mixed as needed.

Of these, water or an aqueous solution of an inorganic electrolyte is fed after a sheet product has been molded.

The heat-fusible adhesive powder used in the present invention is an adhesive that fuses under heat and pressure and that is selected with consideration for the softening point, grain size, bonding method, miscibility with the powdered warming composition, adhesion to nonwoven fabrics, and the like.

The following are examples of such a heat-fusible adhesive powder: ethylene/vinyl acetate copolymers, ionomers, and other copolymers; homopolymers or polymer blends of thermoplastic resins such as polyethylene, polypropylene, polystyrene, polyvinyl alcohol, methyl cellulose, and ethyl cellulose; hot-melt adhesive powders containing such thermoplastic resins as base polymers and further containing admixed tackifiers, waxes, and the like. These adhesive powders may be used individually or as mixtures.

The softening point of the heat-fusible adhesive powder should preferably be 40–200° C.

In terms of diameter, the grain size of the heat-fusible adhesive powder is commonly 0.02–2 mm, preferably 0.05–1.5 mm, and ideally 0.1–0.8 mm.

The amount in which the heat-fusible adhesive powder is added varies with the addition method and cannot be defined unconditionally, but is commonly 0.1–20 parts by weight, preferably 0.3–12 parts by weight, and ideally 0.5–7 parts by weight, per 100 parts by weight of the oxidizable metal powder.

A method for manufacturing the sheet shaped heat generating body pertaining to the present invention will now be described with reference to FIG. 1, but the present invention is not limited by this example.

Water or an adhesive is applied to a nonwoven fabric (a) 2 in a water or adhesive applicator unit 5 in FIG. 1.

The adhesive or water can be applied by spraying, impregnating with the aid of rolls, or the like. It is also possible to use a nonwoven fabric that has been coated with an adhesive in advance during fabrication.

The adhesive or water may be applied uniformly over the entire surface, or it may be applied to selected portions, forming a dot pattern, a lattice, or the like. In addition to being applied to the lower surface of the nonwoven fabric (a), the adhesive or water may also be applied to the upper surface of the nonwoven fabric (b) or to the two surfaces of the nonwoven fabrics (a) and (b). Examples of adhesives that can be applied to the nonwoven fabric (a) include solution-type adhesives, emulsion-type adhesives, hot-melt adhesives, reactive adhesives, and pressure-sensitive adhesives.

Water is applied in an amount that is commonly 5–200 g/m², and preferably 10–120 g/m². The adhesive is applied in an amount that is commonly 0.5–100 g/m², and preferably 2–50 gm², in terms of solids concentration.

The step in which the nonwoven fabric (a) is superposed and a powdered warming composition and a heat-fusible adhesive powder are spread will now be described with reference to FIG. 1.

The nonwoven fabric (a) 2 coated with water or an adhesive is superposed on the nonwoven fabric (b) with the aid of a roller unit 6. The powdered warming composition and the heat-fusible adhesive powder are then spread with the aid of a unit 7 for packing a powdered warming composition and with the aid of a unit 8 for spreading a heat-fusible adhesive powder, and the composition and the powder are retained in the voids and on the upper surface of the nonwoven fabric (a) 2.

The following methods can be used for spreading the heat-fusible adhesive powder in addition to the methods in which the powdered warming composition is spread over the aforementioned nonwoven fabric (a), and the heat-fusible adhesive powder is then spread on top thereof: methods in which the heat-fusible adhesive powder is mixed with the powdered warming composition and spread over the nonwoven fabric (a), methods in which the powdered warming composition is spread following the spreading of the heat-fusible adhesive powder, and methods in which the heat-fusible adhesive powder is spread before and after the powdered warming composition is spread. However, methods in which the heat-fusible adhesive powder and the powdered warming composition are mixed and spread, and methods in which the powdered warming composition is spread following the spreading of the heat-fusible adhesive powder are preferred because methods in which the heat-fusible adhesive powder is spread prior to the spreading of the powdered warming composition creates the danger that a heat-fusible adhesive powder having a certain grain size will clog the mesh of the nonwoven fabric (a) or will pass through the nonwoven fabric (a).

When the heat-fusible adhesive powder is spread following the spreading of the powdered warming composition, the spreading may be performed either uniformly over the entire surface or partially in a dot pattern, in a lattice pattern, or the like.

Examples of methods for holding a powdered warming composition or a mixture of a powdered warming composition and a heat-fusible adhesive powder in the voids of the nonwoven fabric (a) include (1) methods in which a mixture of an oxidizable metal powder, activated carbon, an inorganic electrolyte, a heat-melting adhesive powder, and the like is spread over the nonwoven fabric (a) and shaken, penetrating into the voids and remaining there, and (2) methods in which a mixture of an oxidizable metal powder, activated carbon, a heat-fusible adhesive powder, and the like (with the exception of the inorganic electrolyte) is spread over the nonwoven fabric (a) and shaken, penetrating into the voids and remaining there, and an aqueous solution of the inorganic electrolyte is spread following sheet molding. In methods 1 and 2, shaking may be substituted with dispersing and retaining the powders by applying suction from underneath the nonwoven fabric (a).

Of these, methods 2 are preferred from the standpoint of being able to uniformly disperse the inorganic electrolyte over the entire fabric.

The amount in which the warming composition is retained by the nonwoven fabric is determined in accordance with the thickness of the nonwoven fabric, the thickness of the target warmer, the desired heat-generation performance, and the like, and is commonly 500–10,000 g, and preferably 1000–5000 g, per 1 m² of support. The warming temperature and the duration of warming decrease when retention is less than 500 g, and the warmer becomes thicker, making it difficult to form a thin, flexible sheet, when retention exceeds 10,000 g.

Steps in which the nonwoven fabric (c) is superposed, heated/compressed, cut, and coated with an aqueous solution of an inorganic electrolyte will now be described with reference to FIG. 1.

A nonwoven fabric (c) 10 is superposed with the aid of a roller unit 11 on a laminate comprising a nonwoven fabric (b) 4 and a nonwoven fabric (a) 2 on which a powdered warming composition and a heat-fusible adhesive powder have been spread and supported, and the assembly is heated and compressed by a heating and compressing apparatus 12 provided with an embossed surface, whereby the heat-fusible adhesive powder melts primarily in the areas in contact with the protrusions on the heating and compressing apparatus, partially bonding the nonwoven fabric (a) 2 and the nonwoven fabric (c) 10. The resulting product is subsequently cut into the desired sizes by a cutting unit 13 and coated with water or an aqueous solution of an inorganic electrolyte by a unit 14 for spreading water or aqueous solutions of inorganic electrolytes. A sheet shaped heat generating body 15 is thus obtained.

The heating and compressing can be performed by passing the assembly through a heating press or between heating rolls. The heating and compressing can also be performed with planar or smooth rolls, but those in which at least one pressure surface is embossed should preferably be used in order to improve the forming and fixing effect while preserving the flexibility of the sheet product. The bosses are not subject to any particular limitations in terms of shape and are commonly patterned as waves, tortoise shells, rings, drops of water, meshes, or the like. It is preferable to use a shape that facilitates the melting of the powdered warming composition in the non-protruding portions during heating and pressing.

The ratio of the surface area of the bosses to the entire pressure surface is not subject to any particular limitations, and is commonly 0.5–60.0%, and preferably 5.0–40.0%.

The temperature and pressure conditions of heating and pressing vary with the material of the nonwoven fabrics (a), (b), and (c), the softening temperature of the heat-fusible adhesive powder, and the amount in which the powdered warming composition is retained. In the case of heating rollers, for example, the temperature is commonly 70–300° C., and the linear load about 0.1–250 kg/cm. As a result, the heat-fusible adhesive powder in contact with the protrusions melts and acquires a fixed shape while the laminate is compressed, yielding a thin sheet product.

The thickness of the sheet shaped heat generating body is selected depending on the desired heat-generation performance, application, and the like, but should be set as low as possible in order to utilize the characteristics of the product as a sheet: commonly 6 mm or less, and preferably 4 mm or less. In addition, the product is cut into the appropriate shapes and sizes in accordance with its intended usage.

The amount in which the sheet product is impregnated with water or an aqueous solution of an inorganic electrolyte is expressed in terms of the total amount of water or the aqueous solution of the inorganic electrolyte as a percentage of the warming composition. The water or solution is fed and used for impregnation by means of spraying, dripping, roll impregnation, or the like, yielding a sheet shaped heat generating body.

The sheet shaped heat generating body thus obtained may be used directly or may be placed in a pack or the like made of a laminate film of polyethylene and nonwoven fabric having vent holes, or made of an air-permeable film having micro pores to obtain heat-generation characteristics suited to the intended application, and is then sealed in an air-impermeable pack for storage, yielding a pocket heater, a medical heating pack, or the like.

Figure 2:
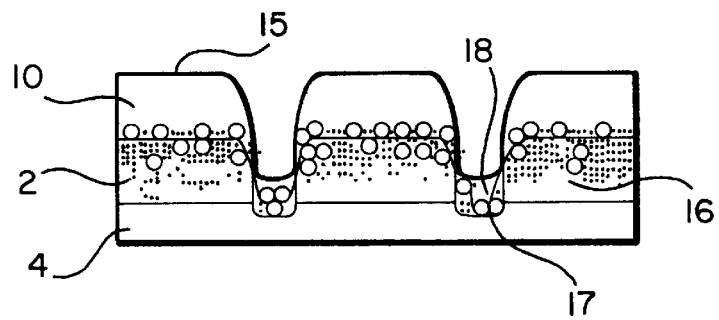
FIG. 2 is a cross section of a sheet shaped heat generating body pertaining to an embodiment of the present invention.

FIG. 2 depicts an example of a cross section of the sheet shaped heat generating body 15 of the present invention. 2 is a nonwoven fabric (a), 4 is a nonwoven fabric (b), 10 is a nonwoven fabric (c), and 16 is a powdered warming composition. 17 is a heat-fusible adhesive powder, and 18 is a portion bonded by the heat-fusible adhesive powder.

FIGS. 1 and 2 depict an example in which three layers of nonwoven fabric are laminated, but the present invention is not limited to this option alone and may involve a two-layer structure of nonwoven fabrics (a) and (b), a laminate having a two-layer structure, a laminate having a three-layer structure, or a laminate which is a combination of a two-layer structure and a three-layer structure.

A two-layer structure comprises layers (a) and (c) of nonwoven fabric, and the manufacturing steps are the same as in the manufacturing method described above, except that the step for bonding the nonwoven fabrics (a) and (b) is omitted. Specifically, a powdered warming composition and a heat-fusible adhesive powder are retained inside the voids by being spread over the upper surface of a nonwoven fabric (a) whose lower surface is optionally covered with adhered water, a nonwoven fabric (c) is superposed on the upper surface of the nonwoven fabric (a), the nonwoven fabrics (a) and (c) are bonded by being heated and compressed with the aid of a heating and compressing apparatus, and the assembly is impregnated with water or an aqueous solution of an inorganic electrolyte.

When a three and/or two-layer structure is laminated, the steps for manufacturing laminates having three and two-layer structures are the same as the methods described above, and the layers of each laminate can be bonded in the same manner as in the case of the nonwoven fabrics (a) and (b), that is, by a bonding method based on the use of water or an adhesive.

Specifically, the present invention includes sheet shaped heat generating bodies obtained by a process in which a plurality of pieces of nonwoven fabric are superposed, a powdered warming composition and a heat-fusible adhesive powder is retained by at least one layer of nonwoven fabric, at least one surface of the other nonwoven fabric in contact with this layer of nonwoven fabric is bonded by being heated and compressed with the aid of a heating and compressing apparatus, and the molded sheet is impregnated with water or an aqueous solution of an inorganic electrolyte.

Thus, an advantage of the present invention is that a powdered warming composition can be dispersed and held in a nonwoven fabric without leakage by bonding the nonwoven fabrics (a) and (c) with the aid of a heat-fusible adhesive powder. Another significant advantage is that the steps that follow impregnation with water or an aqueous solution of an inorganic electrolyte allow a warmer which is pleasant to the touch to be obtained without causing separation between the nonwoven fabrics (a) and (c) while ensuring that the heat-fusible adhesive powder is held securely.

The present invention will now be described in further detail through examples, but the present invention is not limited by these.

EXAMPLE 1

In the apparatus shown in FIG. 1, tissue paper with a weight of 25 g/m$^2$ was fed at a velocity of 2 m/min and superposed onto the following material with the aid of a roller unit while being heated: a wood pulp nonwoven fabric (KINOCLOTH; manufactured by Honshu Paper) which had a thickness of about 1.9 mm, a weight of 57 g/m$^2$, and a porosity of 97.9% and whose lower surface was coated with an ethylene/vinyl acetate-based emulsion adhesive in a dot pattern in a ratio of 10 g/m$^2$.

A mixture comprising 90 parts of iron powder, 8 parts of activated carbon, and 2 parts of a super absorbent polymer (Sumika-Gel S-80; manufactured by Sumitomo Chemical) was subsequently spread over the upper surface of the nonwoven fabric in a ratio of 1100 g/m$^2$; a powdered ethylene/vinyl acetate copolymer resin (H4011-N; manufactured by Sumitomo Seika Chemicals) was spread over the upper surface; and the nonwoven fabric was vibrated in the vertical direction to secure the material in the pores of the nonwoven fabric. A wood pulp nonwoven fabric (KINOCLOTH; manufactured by Honshu Paper) with a thickness of 1.2 mm, a weight of 40 g/m$^2$, and a porosity of 97.5% was subsequently superposed on the upper surface of this nonwoven fabric, the surface of the upper roller was then embossed in a network pattern, and the fabric was fed to a heating and compressing roller apparatus that was set to a temperature of 200° C. and a linear load of 133 kg/cm, yielding a sheet.

This sheet was cut to the dimensions 7.9 cm by 10.4 cm. After this was done, an aqueous saline comprising 8.5 parts of table salt and 91.5 parts of water was spread in a ratio of 600 g/m$^2$, yielding a sheet shaped heat generating body with a thickness of about 1.8 mm. A sheet-shape warmer pack was fabricated by placing this warmer in a flat inner pack in which one side was a composite sheet of a nylon nonwoven fabric and a polypropylene micro porous film with a water vapor transmission of 350 g/m$^2$.day, and the other side was a film laminate composed of a polyethylene film and a nonwoven nylon fabric. In the process, the warmer remained flexible and did not undergo any peeling of the nonwoven fabrics or shedding of the warming composition. The product was then sealed and stored in an air-impermeable outer pack.

Figure 3:
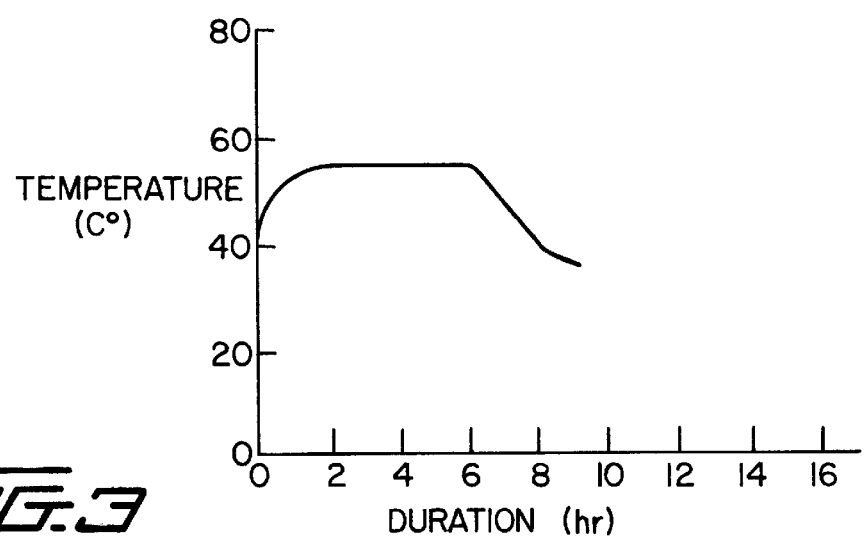
FIG. 3 is a diagram depicting measurement results for the heat-generation characteristics of the sheet shaped heat generating body pertaining to the embodiment of the present invention.

The sheet-shape warmer pack was taken out of the outer pack two days later, and its heat-generation performance was measured in a chamber with room temperature (20° C.) and a relative humidity of 65% in accordance with the heat-generation testing technique described in JIS S4100. As a result, heat-generation characteristics such as those depicted in FIG. 3 were obtained.

Specifically, the temperature exceeded 40° C. in 8.5 minutes, and reached the maximum temperature of 52° C. in 70 minutes. The duration of warming at 40° C. or higher was about 8 hours.

In addition, the sheet-shape warmer pack continuously provided a comfortable temperature for a period of about 10 hours and remained a flexible sheet throughout this period when taken out of the outer pack and worn on the body.

EXAMPLE 2

In the apparatus shown in FIG. 1, tissue paper with a weight of 25 g/m$^2$ was fed at a velocity of 2 m/min and superposed onto the following material with the aid of a roller unit: a wood pulp nonwoven fabric (KINOCLOTH; manufactured by Honshu Paper) which had a thickness of about 1.9 mm, a weight of 57 g/m$^2$, and a porosity of 97.9% and whose lower surface was completely covered with water in a ratio of 12 g/m$^2$.

A mixture comprising 90 parts of iron powder, 8 parts of activated carbon, 2 parts of a super absorbent polymer (Sumika-Gel S-80; manufactured by Sumitomo Chemical), and 1 part of a powdered ethylene/vinyl acetate copolymer resin (H4011-N; manufactured by Sumitomo Seika Chemicals) was spread over the upper surface of the nonwoven fabric in a ratio of 1100 g/m$^2$, and the nonwoven fabric was vibrated in the vertical direction to secure the material in the pores of the nonwoven fabric. A wood pulp nonwoven fabric (KINOCLOTH; manufactured by Honshu Paper) with a thickness of 1.2 mm, a weight of 40 g/m$^2$, and a porosity of 97.5% was subsequently superposed on the upper surface of this nonwoven fabric; the surface of the upper roller was then embossed in a network pattern; and the fabric was fed to a heating and compressing roller apparatus that was set to a temperature of 200° C. and a linear load of 133 kg/cm, yielding a sheet.

This sheet was cut to the dimensions 7.9 cm by 10.4 cm. After this was done, an aqueous saline comprising 8.5 parts of table salt and 91.5 parts of water was spread in a ratio of 600 g/m$^2$, yielding a sheet shaped heat generating body with a thickness of about 1.8 mm. A sheet-shape warming pack was fabricated by placing this warmer in a flat inner pack in which one side was a composite sheet of a nylon nonwoven fabric and a polypropylene micro porous film with a water vapor transmission of 350 g/m$^2$.day, and the other side was a film laminate composed of a polyethylene film and a nonwoven nylon fabric. In the process, the warmer remained flexible and did not undergo any peeling of the nonwoven fabrics or shedding of the warming composition. The product was then sealed and stored in an air-impermeable outer pack.

The sheet-shape warmer pack was taken out of the outer pack two days later, and its heat-generation performance was measured in a chamber with room temperature (20° C.) and a relative humidity of 65% in accordance with the heat-generation testing technique described in JIS S4100. As a result, the temperature exceeded 40° C. in 8.0 minutes, and reached the maximum temperature of 52° C. in 75 minutes. The duration of warming at 40° C. or higher was about 8 hours.

In addition, the sheet-shape warmer pack continuously provided a comfortable temperature for a period of about 10 hours and remained a flexible sheet throughout this period when taken out of the outer pack and worn on the body.

EXAMPLE 3

A wood pulp, nonwoven fabric (KINOCLOTH; manufactured by Honshu Paper) which had a thickness of about 1.9 mm, a weight of 57 g/m$^2$, and a porosity of 97.9% and whose lower surface was completely covered with water in a ratio of 12 g/m$^2$ was fed at a velocity of 2 m/min; a mixture comprising 90 parts of iron powder, 8 parts of activated carbon, 2 parts of a super absorbent polymer (Sumika-Gel S-80; manufactured by Sumitomo Chemical), and 1 part of a powdered ethylene/vinyl acetate copolymer resin (H4011-N; manufactured by Sumitomo Seika Chemicals) was spread over the upper surface of the nonwoven fabric in a ratio of 1100 g/m$^2$; and the nonwoven fabric was vibrated in the vertical direction to secure the material in the pores of the nonwoven fabric. A wood pulp nonwoven fabric (KINOCLOTH; manufactured by Honshu Paper) with a thickness of 1.2 mm, a weight of 40 g/m$^2$, and a porosity of 97.5% was subsequently superposed on the upper surface of this nonwoven fabric; the surface of the upper roller was then embossed in a network pattern; and the fabric was fed to a heating and compressing roller apparatus that was set to a temperature of 200° C. and a linear load of 133 kg/cm, yielding a sheet.

This sheet was cut to the dimensions 7.9 cm by 10.4 cm. After this was done, an aqueous saline comprising 8.5 parts of table salt and 91.5 parts of water was spread in a ratio of 600 g/m$^2$, yielding a sheet shaped heat generating body with a thickness of about 1.7 mm. A sheet-shape warmer pack was fabricated by placing this warmer in a flat inner pack in which one side was a composite sheet of a nylon nonwoven fabric and a polypropylene micro porous film with a water vapor transmission of 350 g/m$^2$.day, and the other side was a film laminate composed of a polyethylene film and a nonwoven nylon fabric. In the process, the sheet shaped heat generating body remained flexible and did not undergo any peeling of the nonwoven fabrics or shedding of the warming composition.

In addition, the sheet-shape warmer pack continuously provided a comfortable temperature for a period of about 10 hours and remained a flexible sheet throughout this period when taken out of the outer pack and worn on the body.

INDUSTRIAL APPLICABILITY

The present invention makes it possible to obtain a sheet shaped heat generating body which is flexible, in which the pieces of nonwoven fabric are securely bonded, and in which the powdered warming composition does not leak. In addition, processes subsequent to impregnation with water or an aqueous solution of an inorganic electrolyte prevent the layers of nonwoven fabrics (a) and (c) from separating from each other, allows the powdered warming composition to be securely supported, and yields an warmer which is pleasant to the touch.

What is claimed is:

1. A sheet shaped heat generating body, comprising a layer of nonwoven fabric (b) superposed on a lower surface of a layer of nonwoven fabric (a) having numerous voids, and a layer of nonwoven fabric (c) superposed on an upper surface of the nonwoven fabric (a), a powdered warming composition and a heat-fusible adhesive powder disposed in the voids of the nonwoven fabric (a) and between the superposed layers of the nonwoven fabric (a) and nonwoven fabric (c), wherein the nonwoven fabric (a) and nonwoven fabric (c) are partially bonded by a plurality of fused areas of said heat-fusible adhesive powder and the body is impregnated with water or an aqueous solution of an inorganic electrolyte.

2. A sheet shaped heat generating body, comprising a powdered warming composition and a heat-fusible adhesive powder held in voids of a layer of nonwoven fabric (a) and a layer of nonwoven fabric (c) and between superposed layers of the nonwoven fabric (a) and nonwoven fabric (c), the layers of nonwoven fabric (a) and nonwoven fabric (c) being partially bonded by a plurality of fused areas of said heat-fusible adhesive powder the body being impregnated with water or an aqueous solution of an inorganic electrolyte.

3. A sheet shaped heat generating body, comprising a plurality of superposed layers of nonwoven fabric, at least one of which has numerous voids on at least one side, a powdered warming composition and a heat-fusible adhesive powder disposed in said voids of said at least one layer of nonwoven fabric, wherein said void possessing side of said at least one fabric layer is partially bonded to one of the other layers of nonwoven fabric by a plurality of fused areas of said heat-fusible adhesive powder and the body is impregnated with water or an aqueous solution of an inorganic electrolyte.

4. A sheet shaped heat generating body as defined in claim 1, wherein the heat-fusible adhesive powder is at least one resin powder selected from the group consisting of homopolymers of thermoplastic resins selected from the group consisting of ionomers, ethylene/vinyl acetate copolymers, polyethylene, polypropylene, polystyrene, polyvinyl alcohol, methyl cellulose, and ethyl cellulose; polymer blends of these thermoplastic resins; and hot melts containing these thermoplastic resins as their base polymers.

5. A sheet shaped heat generating body as defined in claim 1, wherein the softening point of the heat-fusible adhesive powder is 40–200° C.

6. A sheet shaped heat generating body as defined in claim 1, wherein the amount in which the heat-fusible adhesive powder is added is 0.1–20.0 parts by weight per 100 parts by weight of an oxidizable metal powder.

7. A sheet shaped heat generating body as defined in claim 1, wherein the powdered warming composition contains an oxidizable metal powder and activated carbon, or an oxidizable metal powder, activated carbon, and an inorganic electrolyte as its principal components.

8. A sheet shaped heat generating body as defined in claim 1, wherein said fused areas of said heat-fusible adhesive powder forms an embossed pattern.

9. A sheet shaped heat generating body as defined in claim 1, wherein the nonwoven fabrics (a), (b), and (c) have at least one component selected from the group consisting of pulp, cotton, jute, rayon, and acetate as their principal component.

10. A method for manufacturing a sheet shaped heat generating body, comprising the steps of superposing a nonwoven fabric (b) on a lower surface of a nonwoven fabric (a) having numerous voids, bonding these nonwoven fabrics using water or an adhesive, spreading a powdered warming composition and a heat-fusible adhesive powder over an upper surface of the nonwoven fabric (a) and and into said numerous voids, superposing a nonwoven fabric (c) on the upper surface of the nonwoven fabric (a), and bonding the nonwoven fabric (a) and nonwoven fabric (c) by heating and compressing selected areas of fabric (c) to fuse areas of said heat-fusible adhesive powder and impregnating the body with water or an aqueous solution of an inorganic electrolyte.

11. A method for manufacturing a sheet shaped heat generating body, comprising the steps of spreading a powdered warming composition and a heat-fusible adhesive powder over an upper surface of a nonwoven fabric (a) which has numerous voids, superposing a nonwoven fabric (c) over the upper surface of the nonwoven fabric (a), and bonding the nonwoven fabric (a) and nonwoven fabric (c) by heating and compressing selected areas of fabric (c) to fuse areas of said heat-fusible adhesive powder.

12. A method for manufacturing a sheet shaped heat generating body as defined in claim 10, wherein the heat-fusible adhesive powder is at least one resin powder selected from the group consisting of homopolymers of thermoplastic resins selected from the group consisting of ionomers, ethylene/vinyl acetate copolymers, polyethylene, polypropylene, polystyrene, polyvinyl alcohol, methyl cellulose, and ethyl cellulose; polymer blends of these; and hot melts containing these, thermoplastic resins as their base polymers.

13. A method for manufacturing a sheet shaped heat generating body as defined in claim 10, wherein the softening point of the heat-fusible adhesive powder is 40–200° C.

14. A method for manufacturing a sheet shaped heat generating body as defined in claim 10, wherein the amount in which the heat-fusible adhesive powder is added is 0.2–20.0 parts by weight per 100 parts by weight of an oxidizable metal powder.

15. A method for manufacturing a sheet shaped heat generating body as defined in claim 10, wherein the powdered warming composition contains an oxidizable metal powder and activated carbon, or an oxidizable metal powder, activated carbon, and an inorganic electrolyte as its principal components. of pulp, cotton, jute, rayon, and acetate as their principal component.

16. A method for manufacturing a sheet shaped heat generating body as defined in claim 10, wherein said selected areas form an embossed pattern.

17. A method for manufacturing a sheet shaped heat generating body as defined in claim 10, wherein the nonwoven fabrics have at least one component selected from the group consisting of pulp, cotton, jute, rayon, and acetate as their principal component.

* * * * *